United States Patent [19]

Lafferty

[11] 4,138,291

[45] Feb. 6, 1979

[54] MICROBIOLOGICAL METHODS

[75] Inventor: Robert M. Lafferty, Graz, Austria

[73] Assignee: Agroferm AG, Chur, Switzerland

[21] Appl. No.: 822,756

[22] Filed: Aug. 8, 1977

[30] Foreign Application Priority Data

Aug. 6, 1976 [CH] Switzerland .................. 10104/76

[51] Int. Cl.² .............................................. C12D 1/02
[52] U.S. Cl. ...................................... 195/47; 195/79; 195/112
[58] Field of Search ................. 195/47, 79, 112, 101

[56] References Cited

U.S. PATENT DOCUMENTS

| 2,439,572 | 4/1948 | Levin | 195/79 |
|---|---|---|---|
| 3,044,942 | 7/1962 | Baptist | 195/47 |
| 3,071,518 | 1/1963 | Scherr et al. | 195/47 |
| 3,072,538 | 1/1963 | Baptist | 195/101 |

*Primary Examiner*—Alvin E. Tanenholtz
*Attorney, Agent, or Firm*—Sughrue, Rothwell, Mion, Zinn and Macpeak

[57] ABSTRACT

The invention relates to a method of obtaining selected bacterial strains which can convert an assimilable carbon source selected from carbohydrates, methanol, ethanol, glycerin, carbon dioxide and spent lyes from caprolactam synthesis into poly-(D-3-hydroxybutyric acid), selected bacterial strains obtained thereby and their use in producing poly-(D-3-hydroxybutyric acid).

26 Claims, 1 Drawing Figure

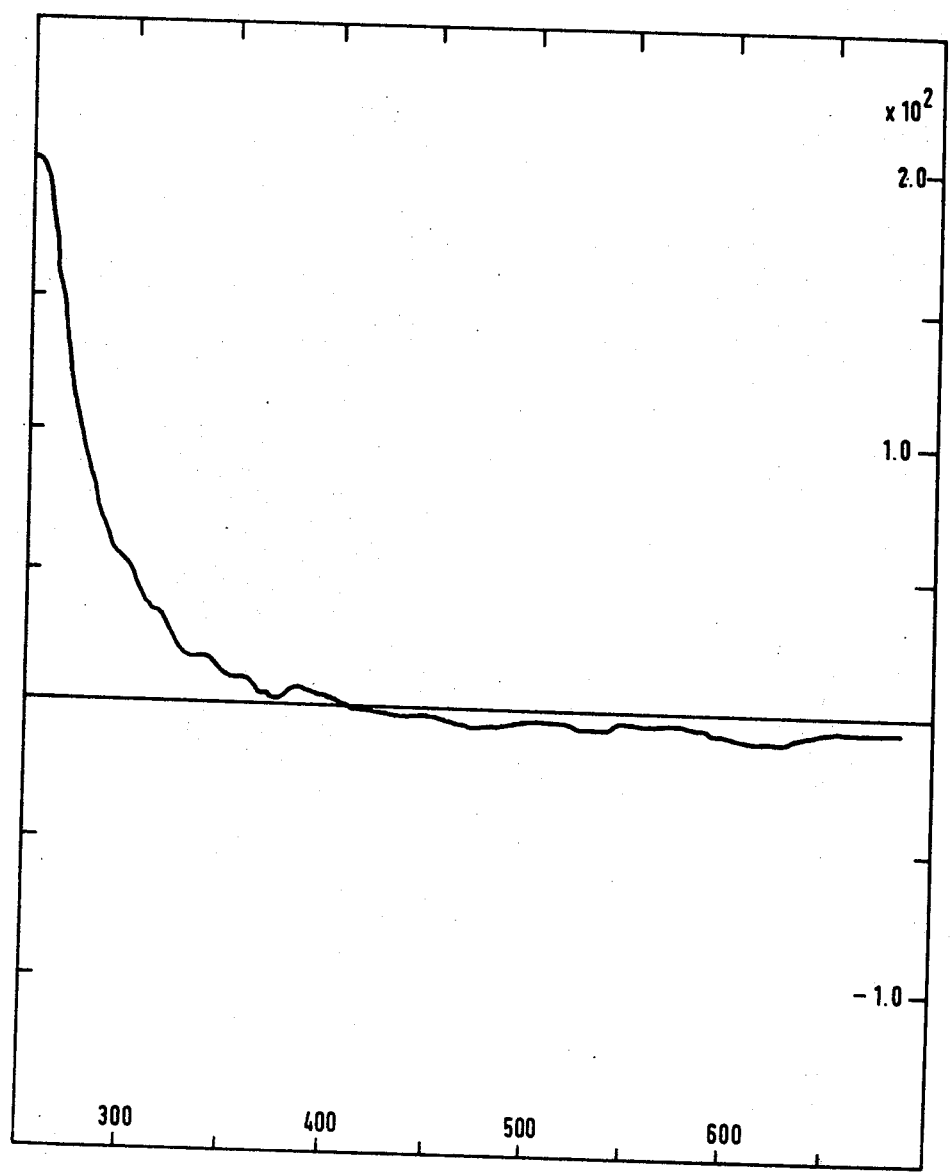

MICROBIOLOGICAL METHODS

The present invention relates to a method of obtaining new bacterial strains which are capable of producing microbiologically on a large scale, poly-(D-3-hydroxybutyric acid) from cheap, abundant raw materials. Poly-(D-3-hydroxybutyric acid) can be processed, among other things, to manufacture structures and moulded bodies such as, for example, threads, fibres and films which are biodegradable.

Synthetic, high molecular weight polymers are presently in widespread use because of their desirable physical and chemical properties and the ease with which they can be formed. The presently known polymers obtained chemicosynthetically are, however, hampered by a large number of serious disadvantages. Their monomeric starting materials are almost without exception obtained from fractions in petroleum cracking or from coal processing. Such starting materials include, for example, linear hydrocarbons e.g. ethylene and propylene, cyclic hydrocarbons e.g. cyclohexane and their reaction products, such as e.g. ethylene oxide and cyclohexanone. As is known the sources for such starting materials of chemico-synthetic polymers are limited and are still used for other purposes important to life. Thus such resources are subject to an increasing shortage.

A further disadvantage of chemico-synthetic polymers is that they impose a strain on the environment. Firstly, they can be eliminated only by burning, in which case large amounts of carbonaceous material and undesirable carbon monoxide and carbon dioxide are usually generated. In addition, burning of a large number of plastics leads to extremely harmful side products, such as, for example, hydrochloric acid, ammonia, nitrogen oxides and benzopyrene, which, it has been proved, are highly corrosive or even disease-inducing (e.g. cancer) and, consequently, are extremely detrimental to the environment. Because the consumption of synthetic plastics has reached substantial proportions, their elimination places an enormous strain on public incinerator installations. Finally, the chemico-synthetic manufacture of polymeric substances entails, without exception, the formation of dangerous intermediate products which are sometimes highly toxic and/or explosive, which is why increasingly expensive precautions on the production line are demanded by the authorities.

In the present invention we have found a way of manufacturing polymers from abundant starting materials, such as carbon dioxide or carbohydrates, or originating from substances which represent waste products prejudicial to the environment, such as e.g. spent lye containing carboxylic acids from caprolactam synthesis.

Thus according to the present invention there is provided a method of obtaining selected bacterial strains which can substantially convert an assimilable carbon source selected from carbohydrates, methanol, ethanol, glycerin, carbon dioxide and spent lyes from caprolactam synthesis containing monocarboxylic and dicarboxylic acids into poly-(D-3-hydroxybutyric acid) which method comprises selecting from poly-(D-3-hydroxybutyric acid) — producing bacterial strains those which form colonies of milky-white appearance on an agar nutrient medium, said colonies having dome-shaped elevations above the agar surface or attaining large dimensions; breeding said selected bacterial strains on constantly increasing concentrations of said assimilable carbon source; and subjecting said bacterial strains at least once, either before, after or during selection and/or breeding, to the action of mutagenic agents whereby the desired bacterial strains are obtained. The bacterial strains thus obtained may then be used to produce poly-(D-3-hydroxybutyric acid) by culturing them on the said assimilable carbon source.

The steps necessary to manufacture the polymeric material can be effected under safe conditions which are non-detrimental to the environment. Furthermore, the polymers manufactured according to the invention are biodegradable, products such as films made from them being dissolved completely within weeks or months by normal arable soil. In fact, substantially all soils contain sufficient microorganisms to split the polyester poly-(D-3-hydroxybutyric acid) and to assimilate the resulting D-3-hydroxybutyric acid.

In spite, however, of this ubiquitous biodegradability, structures produced from the polymers manufactured according to the invention have proved to have a high resistance to acids, alkalis, light, air and most organic solvents.

Polyesters of D(-)-3-hydroxybutyric acid (abbreviation poly-β-hydroxybutyric acid or PHB) have the formula:

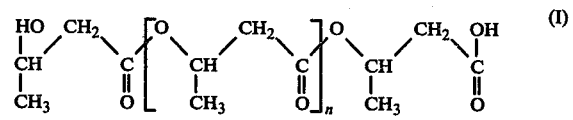

in which n is approximately 6–8,000.

According to the method of the present invention bacterial strains be obtained, which under any growth conditions, can substantially convert an assimilable carbon source which is a spent lye of caprolactam synthesis, (containing monocarboxylic and dicarboxylic acids), a carbohydrate, methanol, ethanol, glycerin or carbon dioxide into poly-(D-3-hydroxybutyric acid).

By growing the selected bacterial strains on increasing concentrations of the assimilable carbon source, the bacteria become adapted to the assimilation of high concentrations of this carbon source.

In addition to the selection procedure described above it is desirable that the bacterial strains are further subjected to one or both of the following two selection procedures, which two procedures may be carried out after the above-described selection procedure in either order:

(a) selection of bacterial strains having the lowest specific weight under conditions which hinder or do not help the microbiological synthesis of poly-(D-3-hydroxybutyric acid), (b) selection of bacterial strains having the strongest colouring after brief flooding with a solution of Sudan black B.

It should be emphasized that the two selection procedures (a) and (b) represent optional, yet particularly advantageous measures. If they are applied, individually or in succession, in addition to the first selection based on the appearance of the colonies formed, they enable, in fact, a quicker selection of bacterial strains of maximum yield in respect of PHB production to be made.

The bacterial strains are preferably subjected to the action of mutagenic agents more than once. The stage at which the treatment or treatments are carried out is not critical and thus, for example, treatment may take place before the selection on the basis of the appearance of the colonies and/or afterwards, or, also, before and/or after the adaptation of the selected bacterial strains to the special carbon source.

If required, it is also possible, in an additional step, to further select from the bacterial strains selected and adapted as described above, those which, in comparison with production by the original strain before adaptation, convert a larger proportion of the carbon source into poly-(D-3-hydroxybutyric acid). This further, optional selection step is based on calculating the carbon transference, i.e. the percentage utilisation of the carbon source in relation to its carbon content. Strains selected in this way, in consuming the carbon source, use only a minimum portion for metabolism and synthesis of the remaining cellular material and thus lead to a higher conversion into PHB: consequently, they have special practical importance.

Likewise, it is possible to further select those bacterial strains which do not or only slightly depolymerise the poly-(D-3-hydroxybutyric acid) or which do not utilise the monomeric D-3-hydroxybutyric acid. It has been shown that, of the mutants or strains producing PHB, those which cannot or can no longer synthesise the enzyme D-(-)-β-hydroxybutyric acid dehydrogenase (EC 1.1.1.30; see E. T. Barman, Enzyme Handbook, Springer-Verlag, Berlin, 1969) are, in general, substantially more constant in their production. Maintenance of the intra-cellular-formed amount of PHB at a constant level over long periods of time is probably due to the absence of depolymerisation.

This further selection step may be carried out by breeding the strains on an agar nutruent medium which contains, as the carbon source a mixture of a very small proportion of an assimilable carbohydrate and a predominant proportion of DL-3-hydroxybutyric acid, conveniently in the form of the sodium salt. Two sorts of colony develop on the medium, one sort sonsisting of very small colonies of differing appearance of approximately a ¼ to 1mm diameter and the other sort of colonies of normal size. The first sort correspond to the desired strains which cannot assimilate or utilise D-3-hydroxybutyric acid, but produce PHB; they have, therefore, generally a milky-like appearance.

As is known, a considerable number of aerobic schizomycetes produce PHB as an energy reserve material either when they receive a surplus of carbon or suffer a lack of nitrogen or when they are exposed to low oxygen concentrations, i.e. bred under conditions favourable to the synthesis of PHB. According to the present invention microorganisms can be found, which always produce, even under conditions prejudicial to PHB synthesis yet optimum for other life processes, large quantities of PHB from economically favourable carbon sources not known or used hitherto for this purpose, such as carbohydrates (e.g. molasses, glucose, fructose, saccharose, lactose), carbon dioxide, methanol, ethanol, glycerin and spent lyes of caprolactam synthesis (hereinafter designated by the abbreviation CAL). Such microorganisms will always produce PHB even under conditions unfavourable to PHB synthesis, such as, for example, wrong C/N ratios or high oxygen partial pressures. After previously known PHB producers had been treated with mutagenic agents, it was possible to select, on the basis of special morphological features, mutants which produce PHB constitutively, i.e. irrespective of the conditions, such as, for example lack of nitrogen, which influence the metabolism of the carbon. Through repeated mutation and selection, microbial strains may be obtained, which form on the above-mentioned carbon sources PHB in a quantity of up to 90% of their cellular dry weight.

Preferred bacterial strains which may be obtained by the method of the present invention include strains derived from *Alcaligenes eutrophus* ATCC 23440, e.g. the mutant CBS 388.76 (GD-5); from *Bacillus megatherium* ATCC 32, e.g. the mutants CBS 389.76 (GB-1003) and CBS 390.76 (GBM-13); from *Zoogloea ramigera* ATCC 19623, e.g. the mutant CBS 391.76 and from *Mycoplana rubra*, e.g. the mutant CBS 385.76.

According to a further feature of the present invention there is provided a method of producing poly-(D-3-hydroxybutyric acid) which comprises culturing a selected bacterial strain as hereinbefore defined in the presence of an assimilable carbon source selected from carbohydrates, methanol, ethanol, glycerin, carbon dioxide and spent lyes from caprolactam synthesis containing monocarboxylic and dicarboxylic acids, an assimilable nitrogen source and trace elements, and isolating the poly-(D-3-hydroxybutyric acid) thus produced from the culture medium. Although PHB can be produced both in a surface culture and in a submerged culture, the latter is preferred on a large scale.

The chain length (n in formula I) is largely determined by the choice of the extraction method used to isolate polymers from the culture medium. Polar solvents, e.g. ethanol, mainly leads to the extraction of polymers with smaller molecular weights and lower melting points, while lipophilic solvents are more selective for higher molecular polymers with e.g. n = 80–110 and melting points from 150° C. to 190° C. By various treatments of the culture medium, such as e.g. enzymatic lysis and treatment with alkalis or mineral acids, it is possible not only to improve the extractability of the polymers, but also to influence their fractionation according to molecular size. Preferred solvents for the extraction of PHB from the natural culture medium are ethylene carbonate and propylene carbonate. Both solvents are suitable for the continuous extraction of PHB from a liquid culture medium and, moreover, enable the molecular weight of the PHB obtained to largely depend on the extraction temperature and extraction period. Thus, PHB may be obtained having a molecular weight above 1,000,000 with, for example propylene carbonate at 120° C. and an extraction time of 1–5 minutes, while PHB having a molecular weight of approximately 30,000–200,000 may be obtained, for example, with ethylene carbonate at 110° C. and an extraction time of 1–10 minutes. By extraction with ethylene carbonate or propylene carbonate at higher temperature and/or using longer extraction times, it is possible to obtain PHB molecules of even smaller chain length. By cooling these solutions pure PHB may be precipitated, which can easily be separated.

To change the physical properties of the PHB, the PHB molecules can be esterified under conditions assisting esterification (especially dehydrating measures), so that a polymeric substance with larger molecular weights, i.e. a multiplied claim length of I arises. As a result, polymers are obtained with improved mechanical properties.

The products can be processed by methods generally known in plastics processing, such as e.g. immersion, rolling, pressing, extrusion, injection moulding, etc., into fibres, films or workpieces or can be processed from solutions or used as lacquers.

Quantitative determination of poly-(D-3-hydroxybutyric acid) and determination of the molecular weight of the products may be carried out as follows:

The polymer (PHB) is hydrolysed and simultaneously dehydrated with concentrated sulphuric acid into crotonic acid (J. H. Law and R. A. Slepecky, J. Bact. 82 (1961),33) which has an absorption maximum in the ultra-violet at 235 nm. For the quantitative determination of PHB, 5 ml of the fermented solution are centrifuged for 10 minutes at approximately 15,000 revolutions per minute. Without disturbing the sediment the supernatant is decanted off and 5 ml of sodium hypochlorite solution are added to the sediment. After thorough mixing the suspension obtained is kept for 1 hour at 37° C., with occasional shaking. It is then filtered through a cellulose folded filter and thoroughly washed with water.

The filter together with the residue is washed with approximately 10 ml acetone and then approximately 10 ml ethanol. The filter and solid residue are placed in a 100 ml round-bottomed flask which is filled with 40 ml chloroform. The flask is held in a boiling water bath until the mixture is boiling fast. The filter is then taken out and thoroughly washed with boiling chloroform over a funnel placed in the neck of the flask. The chloroform is then evaporated out of the flask until dryness. To the completely dry flask are added 5.0 ml of concentrated sulphuric acid (analytical grade) which are swirled round the flask surface so as to moisten all the residue. The flask is then sealed with a stopper and kept at 95°–100° C. for at least 10 minutes. During this time hydrolysis and dehydration of the PHB takes place to form crotonic acid. After cooling, a sample of the contents of the flask is diluted, in two or more steps, e.g. 1:10 with water and then 1:10 with sulphuric acid, so as to give a test solution containing at least 90% of the acid. Measurement of the optical density is made in quartz-glass vessels which must be closed with stoppers to prevent the occurrence of troublesome optical inhomogeneities as far as possible. Measurement is made at 235 nm. The concentration of PHB can be calculated from the measured optical density and the $E_{1cm}^{1\%}$ value of 1524.

An approximately 0.5% solution of a preparation of PHB in chloroform had, at 25° C., a flotation constant of $1.56 \times 10^{-13}$ as measured in an ultra-centrifuge (see H. M. Rauen, Biochemisches Taschenbuch, second part, Springer-Verlag, Berlin 1964, page 746), from which an average molecular weight of approximately 10,000 can be calculated.

A qualitative determination of the PHB can be carried out by means of the optical rotational dispersion spectrum. FIG. 1 shows the spectrum of a chloroform solution containing 1.646 g of poly-(D-3-hydroxybutyric acid) per liter.

Rotatory values at:
  690 nm - 5 (beginning)
  625 nm - 10
  437 nm - 2
  409 nm 0
  400 nm 2
  365 nm 7
  254 nm 199 (finish)

The following non-limiting examples serve to illustrate the present invention.

EXAMPLE 1

(A) 500 ml Erlenmeyer flasks each containing 50 ml of nutrient solution including 3% of glucose, 0.5% $KNO_3$, 0.17% $Na_2HPO_4.2H_2O$, 0.13% $KH_2PO_4$, 0.04% $MgSO_4.7H_2O$, 0.002% $FeSO_4.7H_2O$ and 0.001% $MnCl_2.4H_2O$ were autoclaved at 121° C. and then innoculated with a culture of *Bacillus megatherium* NCIB 8508 and shaken excentrically at 28° C. in the presence of air. After incubation of 48 hours the cells were separated from the nutrient solution, washed with $H_2O$ and mutated in a known manner e.g. with ultra-violet light, $NaNO_2$ or nitro-nitroso-methyl guanidine (see e.g. R. C. Clowes and W. Hayes, Experiments in Microbial Genetics, Blackwell Scientific Publications, Oxford and Edinburgh 1968). The surviving cells were spread out on the above medium, with 1.5% agar, so that scattered colonies were obtained. Colonies of a pronounced milky-white appearance, which formed dome-like elevations over the agar surface or attained large dimensions, were selected to test for PHB under submerged conditions.

Other plates with fully developed scattered colonies were stamped with velvet stamps onto two agar plates (see Clowes and Hayes, loc. cit. "Replication Technique"). The first agar plate was flooded with a solution of Sudan black B for a short time (e.g. 1–5 minutes) and, with the naked eye, the colonies which became the most highly coloured were identified. The second agar plate was used to test the replica colonies for PHB productivity. Both selection procedures led to the isolation of *Bacillus megatherium* mutants which stored, in the above medium, considerably higher quantities of PHB than the original strain.

(B1) According to the method described in part A, selected strains were bred under conditions which were known to cause little or no PHB accumulation, i.e. using the medium of part A except that the nitrogen content was increased by 50% (i.e. brought to 0.75% $KNO_3$), the glucose concentration was lowered to 0.5% and the culture was shaken excentrically for 36 hours at 30° C., in order to obtain high concentrations of $O_2$. The cultures thus obtained were centrifuged, washed with $H_2O$ and suspended in approximately 2 ml of a CsCl solution having a specific density of approximately 1.15. This suspension was carefully added to a linear CsCl gradient solution of approximately 40 ml in a 50 ml centrifuge tube of celluloid. The CsCl gradient (see Rauen, loc. cit. page 535) had been made in such a way that the density varied from 1.15 at the top to 1.38 at the bottom. This gradient was centrifuged, together with the cellular suspension, for 20 hours at 5° C. at approximately 250,000 g. As a result, cells not containing PHB or with a low PHB content concentrated in the zones of higher density, while cells with a high PHB contents concentrated near the surface of the gradient solution. On completion of centrifuging, the gradient tubes were pierced at the lowest point by means of a needle, and the gradient solution was allowed to empty out in drops. The drops of the zones with a low CsCl density were laid on agar plates with the nutrient solution of part A, so that after incubation predominantly scattered colonies arose. These were tested in a known manner, as a submerged culture, to check their capacity for PHB formation. In this way, those strains from part A were obtained which constitutively accumulate PHB, i.e. in each growth phase and not only under special conditions assisting the formation of PHB, as is the case with wild types, such as e.g. *Bacillus megatherium* NCIB 8508 and other known wild types.

The same selection successes were achieved using linear saccharose gradients.

(B2) In a similar way to part A and part B1, using the medium of part A, except that the glucose was replaced by 1% fructose and the KNO3 by 0.4% NH4Cl, mutuants which produced PHB constitutively were obtained from *Bacillus megatherium* ATCC 32, *Bacillus megatherium* NCIB 8674, *Pseudomonas* sp. B 79 NCIB 9088 and *Pseudomonas* sp. B 175 NCIB 9089, *P. facilis* ATCC 11228 and ATCC 17695, *P. pseudomallii* ATCC 11668, *Chromatium violaceum* NCIB 8182, *Rhizobium* sp. HCCB 142, *Azotobacter beijerinckii* NCIB 9067, *A. agilis* NCIB 8637, *A. chroococcum* DSM 281, *A. vinelandii* NCIB 8789, *Hydrogenomonas eutropha* ATCC 17699, *Alcaligenes eutrophus* ATCC 23440, *Flavobacterium aquatile* ATCC 11947, *Bacterium in editio* and *Zoogloea ramigera* ATCC 19623.

(C) Mutants of part B2 which produce PHB constitutively, e.g. those of *Alcaligenes eutrophus* ATCC 23440, *Bacillus megatherium* ATCC 32, *Azotobacter chroococcum* DSM 281 and *Zoogloea ramigera* ATCC 19623, were transferred from submerged cultures, 24 hours old, of the liquid medium of part B2 onto the same medium solidified by agar and containing 0.1% by weight of nuetralised CAL. They were incubated at 30° C. until a few colonies had undergone considerable growth. The largest colonies, which were not influenced or were least influenced in growth by the presence of CAL were then transferred, after mutation treatment carried out in a known manner, onto a similar medium which contained only 0.8% fructose, but 0.2% neutralised CAL. This procedure was repeated until each type of bacteria resulted in mutuants which grew well on CAL as the sole carbon source. For adaptation to higher concentrations of CAL, the following technique was appropriate. Bacterial strains were innoculated on agar plates containing fructose and CAL which, under uninhibited growth, would result in dense bacterial fur. The point of a spatula full of the growth-inhibiting mutagenic agent nitro-nitrosomethyl-guanidine was then applied to the centre of such plates which were then incubated until good growth had taken place. Colonies which formed well very close to the mutagenic agent often proved to be better utilisers of CAL.

By continued application of these methods or combination thereof mutants were obtained which could fully utilise even higher concentrations of CAL as the sole carbon source and which formed PHB constitutively. In particular, the mutants GD-5 of *Alcaligenes eutrophus* ATCC 23440 and GB 1003 of *Bacillus megatherium* ATCC 32 were selected for further work, these assimilating 3% and over of neutralised CAL as the sole carbon source.

EXAMPLE 2

In a similar way to Example 1C, mutants producing PHB constitutively were obtained from bacterial strains in 1B2, i.e. those of *Bacillus megatherium* ATCC 32, *Azotobacter chroococcum* DSM 2 1 and *Zoogloea ramigera* ATCC 19623. The bacteria were mutated and selected in such a way that they produced high quantities of PHB on molasses as the sole carbon source. In this way, mutants were bred which grew well on 30–40% molasses and accumalated approximately 80–90% of their cellular dry weight of PHB. In particular, the mutants GBM-13 of *Bacillus megatherium* ATCC 32 and GZ-1018 of *Zoogloea ramigera* ATCC 19623 were used for further work.

EXAMPLE 3

To find methanol-utilising microorganisms, 100 ml of the nutrient solution of Example 1A were placed in a 500 ml beaker, except that instead of the KNO3, 0.4% NH4Cl was used and instead of the glucose 1% methanol. After a few days, the solution became cloudy and, after appropriate dilution with H2O, individual scattered colonies could be produced from it onto agar plates which contained a sterilized methanol medium. Selected sudanophile colonies were then treated in a similar way to the process of Example 1B1 and 1B2. The best strain produced PHB at approximately 81% of its dry cellular weight. This strain was identified by the curator of the National Collection of Industrial Bacteria (Ministry of Agriculture, Fisheries and Food, Torry Research Station, Aberdeen, Scotland) as a *Mycoplana rubra* strain. The strain was submitted to the Central Bureau for Mould Cultures under the title CBS 385.76 and originally named *Bacterium in editio Pl*. It was characterised as follows:

Morphology (GP agar, consisting of 1% glycerin + 1% peptone at PH 7.0 on agar, 6 days at 30° C.). Pleomorphous rods 0.8 × 1.5–5.0 μm cells contain a high percentage of poly-β-hydroxybutyric acid.

All the submerged cultures, i.e. more than 7 days old, contain small quantities of cells with primary cellular branches which are recognisable under a phase-contrast microscope.

Colony (GP agar, 6 days at 30° C.). A pink-coloured pigment, transparent, round, with distinct edges, convex, smooth and shining, diameter 0.5–1.0 mm. Pigmentation intensifies with increasing age. Very poor growth on a blood agar base (OXOID CM 55).

Submerged Growth (GP nutrient solution, consisting of 1% glycerin + 1% peptone at pH 7.0, 6 days at 30° C.). Rather weak growth, forms a surface ring and skin, slightly viscous sediment.

Temperature:
At 10° C. little or no growth
At 15° C. growth
At 30° C. growth
At 37° C. no growth

| Gram straining Negative to variable | |
|---|---|
| Mobility | + |
| Kovacs Oxidase | + |
| Catalase | + |
| Hugh and Leifson (Glucose) OF | — |
| Peptone water carbohydrates: | Acid formation on glycerin. No acid formation on glucose, fructose, maltose, saccharose, lactose, starch or mannitol. |
| Indol Production | — |
| Methyl red | — |
| Voges-Proskauer | — |
| Koser's citrate | — |
| Tryptone | weak NH4+ formation |
| Nitrate reduction | — |
| Urease (Christensen) | + |
| Starch | weak hydrolysis |
| Gelatin | not hydrolysed |
| Casein | not hydrolysed |
| Haemolysis | — |

ANTIBIOTIC SENSITIVITY

Resistant to penicillin, chloramphenicol and polymyxin B; sensitive to streptomycon and tetracyclin. Can utilize methanol but not methane as the sole carbon source.

EXAMPLE 4

The mutant GD-5 (CBS 388.76) was bred at 28° C. and with aeration (0.5 vol/vol. minute air) under agitation in a small fermenter with 20 litres total volume in 5 litres of the medium of Example 1A, except that the $KNO_3$ was replaced by 0.4% $NH_4Cl$ and the glucose by 2% neutralised CAL of the firm Emser Werke in Domat/Ems (Switzerland). The pH value was kept constant at 6.8 by the addition of dilute HCl. The CAL contained approximately 150 g carboxylic acids per liter which had the following composition according to gas-chromatographic analysis of the methyl esters of the carboxylic acids:

| Succinic acid | 6 g/liter |
|---|---|
| Glutaric acid | 9 g/liter |
| Adipic acid | 57 g/liter |
| Acetic acid | 2.5 g/liter |
| Propionic acid | 3 g/liter |
| Butyric acid | 6 g/liter |
| Valeric acid | 28.5 g/liter |
| Caproic acid | 14.5 g/liter | and an undetermined quantity of oxycaproic acid.

The maximum growth rate $\mu_{max}$ amounted to 0.24/hour and the yield constants were:

$\gamma$ (g cellular dry weight/ml CAL)=0.13, i.e.

$\gamma$ (g cellular dry weight/g carboxylic acids)=0.65.

This corresponds to a carbon transference (i.e. utilisation of the carbon source in relation to its carbon content) of 68%, while the parent strain *Alcaligenes eutrophus* ATCC 234400 has a carbon transference of 57%. The culture contained approximately 78% PHB.

EXAMPLE 5

The mutant GD-5 (CBS 388.76) was incubated at 28° C. in a small fermenter in the medium of Example 4, but without the carbon source, and using an aeration rate of 0.11 vol/vol minute of a mixture of 10% $CO_2$, 20% $O_2$ and 70% $H_2$. It was established that the accumulation of PHB followed an exponential course, i.e. parallel to the biomass formation. The PHB formation rate was 3 $\mu$g/minute.mg protein. Under otherwise identical conditions a maximum growth weight $\mu_{max}$ of 0.23/hour and a productivity of 0.46 g cellular dry weight/1. hour with a proportion of 68% PHB was noted with this mutant in a single-stage continuous fermentation in a chemostat (small fermenter).

EXAMPLE 6

In a similar way to Example 4, the procedure was conducted with the mutant GB-1003 (CBS 389.76) when $\mu_{max}$ was 0.25 per hour and $\gamma$ (g cellular dry weight/ml CAL) = 0.14. The culture contained 81PHB.

EXAMPLE 7

The mutant GBM-13 (CBS 390.76) was bred in a 500 ml Erlenmeyer flask with 100 ml of the medium of Example 4, except that the CAL was replaced by 10% beet molasses. Incubation was carried out at 30° C. for 24 hours with shaking. After this time the culture solution contained 2.5 g bacterial dry mass with a PHB content of 85%.

EXAMPLE 8

The mutant GZ-1018 (CBS 391.76) was bred under the same conditions as in Example 7 using 10% beet molasses which contained 51% saccharose. The result was 2.35 g bacterial dry mass with 79% PHB.

EXAMPLE 9

The mutant GD-5 (CBS 388.76) was bred in a similar way to Example 7, except that 3% ethanol was used instead of the beet molasses. Incubation was for 24 hours. 1.1g of cells with a PHB content of 23% could be harvested.

EXAMPLE 10

A bacterial shaking culture is settled out on a centrifuge and the solid matter is washed with water and taken up in approximately 4 ml of physiological common salt solution. After approximately 1 hour, 4 ml of a 0.6 normal sodium acetate buffer of pH 4.6 and 4 ml of a 0.05 normal sodium nitrite solution may be added to produce mutation, and the mixtures obtained are allowed to incubate for a few minutes. After washing, the solid mass of microorganisms is distributed amongst 10 250 ml Erlenmeyer flasks. To each flask is added the nutrient solution of Example 1A, except that, instead of glucose, the solution contains 1-2% of D,L- or D(-)-3-hydroxybutyric acid in the form of its sodium salt. After clouding visibly increases in the flasks, 1 ml per flask of a sterile-filtered solution of 2-1000 $\mu$g/ml potassium penicillin G or 1 ml of a sterile-filtered solution of 30-1000 $\mu$g/ml bacitracin or of 10-2000 $\mu$g/ml phosphonomycin or 5-1000 $\mu$g vancomycin, or combinations of these solutions or of other antibiotics, such as e.g. Colistin sulphate, influencing cell wall formation or the division of microbes are added, depending on the antibiotic sensitivity of the microorganism used. After a certain incubation period, i.e. after approximately 1-16 hours, the antibiotics are washed out of certain flasks or destroyed with penicillinase. After further washing of the biomass, the surviving microorganisms are innoculated into flasks containing a glucose or fructose medium and incubated. After 16-36 hours dilution series are made from each flask and from those dilutions, which contain approximately 50-1000 microorganisms per ml, 0.1 ml are smeared on agar plates to obtain individual scattered colonies. This agar contains as the carbon source 2% natrium DL-3-hydroxybutyrate and 0.008% fructose or glucose as the sole carbon source. After 48 hours very small colonies develop of varying appearance and of approximately ¼-1 mm diameter and colonies of normal size. For confirmation, inocula are transferred from the small colonies by means of sterile dental probes, either onto spots on an agar plate where sodium 3-hydroxybutyrate is the sole carbon source, or onto spots on an agar plate where glucose or fructose is the sole carbon source.

The desired strains, which can no longer assimilate $\beta$-hydroxbutyric acid and yet still produce PHB, are found among those colonies of mutants which are spontaneously present or produced by artificial mutation and which cannot grow on 3-hydroxybutyric acid, but thrive on glucose or fructose and have a milky-white appearance.

EXAMPLE 11

The strain GBM-13 of *Bacillus megatherium* ATCC 32 was irradiated with ultra-violet light and colonies were bred from the surviving cells on agar with the nutrient solution of Example 1A. According to the method of Example 1, good PHB producers were selected and incubated in 500 ml Erlenmeyer flasks with a 100 ml saccharose medium containing a total of 1.68 g carbon, i.e. 4 g saccharose/l, as a shaking culture. On completion of breeding, the resultant cellular dry mass and the total PHB and carbon content were determined. The residual saccharose content in the remaining liquid was also determined. The following results were obtained:

| Strain | Saccharose g/l beginning | end* | Biomass g/l | C in g/l in biomass | g PHB/l |
|---|---|---|---|---|---|
| GBM-13 | 4 | 0.59 | 1.50 | 0.78 | 1.05 |
| Mutant 1 | 4 | 0.9 | 1.52 | 0.795 | 1.0 |

| Strain | C convention in % |
|---|---|
| GBM-13 | 54.5 |
| Mutant 1 | 60.9 |

*Time of stopping breeding, i.e. after 29 hours of incubation.

The strain with the best carbon utilisation was further treated in a similar way to Example 1, in order to produce strains with even better carbon utilisation and still higher PHB contents.

What is claimed is:

1. A method of obtaining selected bacterial strains which, under any growth conditions, can substantially convert an assimilable carbon source selected from carbohydrates, methanol, ethanol, glycerin, carbon dioxide and spent lyes from caprolactam synthesis containing monocarboxylic and dicarboxylic acids into poly-(D-3-hydroxybutyric acid) which method comprises selecting from poly-(D-3-hydroxybutyric acid)-producing bacterial strains those which form colonies of milky-white appearance on an agar nutrient medium, said colonies having dome-shaped elevations above the agar surface or attaining large dimensions; breeding said selected bacterial strains on constantly increasing concentrations of said assimilable carbon source; and subjecting said bacterial strains at least once to the action of mutagenic agents whereby the desired bacterial strains are obtained.

2. A method as claimed in claim 1 wherein the selected bacterial strains are subjected to one of the following selection procedures:
   (a) selection of bacterial strains having the lowest specific gravity under conditions which hinder or do not help the microbiological synthesis of poly-(D-3-hydroxybutyric acid),
   (b) selection of bacterial strains having the strongest colouring after brief flooding with a solution of Sudan black B.

3. A method as claimed in claim 1 wherein, from the selected bacterial strains, those are further selected which convert a higher proportion of the carbon source into poly-(D-3-hydroxybutyric acid) than the original strain.

4. A method as claimed in claim 1 wherein, from the selected bacterial strains, those are further selected which do not or only slightly depolymerise poly-(D-3-hydroxybutyric acid) or which do not utilise monomeric D-3-hydroxybutyric acid.

5. A method as claimed in claim 4 wherein the further selection comprises selecting those strains which form colonies of milky-white appearance of approximately ¼ to 1 mm diameter when cultured on an agar nutrient medium containing, as the carbon source, a mixture consisting essentially of a greatly predominant amount of DL-3-hydroxybutyric acid in combination with a minor amount of assimilable carbohydrate as compared to the amount of said DL-3-hydroxybutyric acid.

6. A method of using the selected bacterial strains obtained by the method according to claim 1 for producing poly-(D-3-hydroxybutyric acid), which comprises culturing said bacterial strains in an aqueous nutrient medium containing an assimilable carbon source selected from carbohydrates, methanol, ethanol, glycerin, carbon dioxide and spent lyes from caprolactam synthesis containing monocarboxylic and dicarboxylic acids, an assimilable nitrogen source and trace elements, and isolating the poly-(D-3-hydroxybutyric acid) thus produced from the culture medium.

7. A method as claimed in claim 6 wherein the culturing is effected under submerged conditions.

8. A method as claimed in claim 1, wherein said bacterial strains are subjected at least once before selection to the action of said mutagenic agents.

9. A method as claimed in claim 1, wherein said bacterial strains are subjected at least once after selection to the action of said mutagenic agents.

10. A method as claimed in claim 1, wherein said bacterial strains are subjected at least once during selection to the action of said mutagenic agents.

11. A method as claimed in claim 1, wherein said bacterial strains are subjected at least once before breeding to the action of said mutagenic agents.

12. A method as claimed in claim 1, wherein said bacterial strains are subjected at least once after breeding to the action of said mutagenic agents.

13. A method as claimed in claim 1, wherein said bacterial strains are subjected at least once during breeding to the action of said mutagenic agents.

14. A method as claimed in claim 1, wherein said bacterial strains are subjected at least once before said selection and at least once before said breeding to the action of said mutagenic agents.

15. A method as claimed in claim 1, wherein said bacterial strains are subjected at least once before said selection and at least once after said breeding to the action of said mutagenic agents.

16. A method as claimed in claim 1, wherein said bacterial strains are subjected at least once before said selection and at least once during said breeding to the action of said mutagenic agents.

17. A method as claimed in claim 1, wherein said bacterial strains are subjected at least once after said selection and at least once before said breeding to the action of said mutagenic agents.

18. A method as claimed in claim 1, wherein said bacterial strains are subjected at least once after said selection and at least once after said breeding to the action of said mutagenic agents.

19. A method as claimed in claim 1, wherein said bacterial strains are subjected at least once after said selection and at least once during said breeding to the action of said mutagenic agents.

20. A method as claimed in claim 1, wherein said bacterial strains are subjected at least once during said selection and at least once before said breeding to the action of said mutagenic agents.

21. A method as claimed in claim 1, wherein said bacterial strains are subjected at least once during said selection and at least once after said breeding to the action of said mutagenic agents.

22. A method as claimed in claim 1, wherein said bacterial strains are subjected at least once during said selection and at least once during said breeding to the action of said mutagenic agents.

23. A method as claimed in claim 1, wherein the selected bacterial strains are subjected to both of the following selection procedures, which procedures may be carried out in optional order:
(a) selection of bacterial strains having the lowest specific gravity under conditions which hinder or do not help the microbiological synthesis of poly-(D-3-hydroxybutyric acid),
(b) selection of bacterial strains having the strongest colouring after brief flooding with a solution of Sudan black B.

24. A method as claimed in claim 4, wherein the further selection comprises selecting those strains which cannot grow on 3-hydroxybutyric acid, but thrive on an assimilable carbohydrate and have a milky-white appearance when cultured on an agar medium.

25. A method as claimed in claim 24, wherein said assimilable carboyhdrate is glucose or fructose.

26. A method as claimed in claim 25, wherein 0.008% glucose or fructose is used in combination with 2% sodium DL-3-hydroxybutyrate.

* * * * *